United States Patent [19]
Liu et al.

[11] Patent Number: 5,312,748
[45] Date of Patent: * May 17, 1994

[54] PROTEASE

[75] Inventors: Chi-Li Liu, Danbury; Carol M. Beck, Bethel; Robert J. Strobel, Jr.; Janet M. Overholt, both of Danbury, all of Conn.

[73] Assignee: Novo Nordisk A/S, Bagsvaerd, Denmark

[*] Notice: The portion of the term of this patent subsequent to May 22, 2007 has been disclaimed.

[21] Appl. No.: 223,788

[22] PCT Filed: Nov. 25, 1987

[86] PCT No.: PCT/DK87/00144
§ 371 Date: Aug. 30, 1988
§ 102(e) Date: Aug. 30, 1988

[87] PCT Pub. No.: WO88/03947
PCT Pub. Date: Jun. 2, 1988

[30] Foreign Application Priority Data
Nov. 25, 1986 [DK] Denmark .............................. 5640/86

[51] Int. Cl.$^5$ ..................... C12P 21/04; C12N 9/98; C12N 9/52; C12N 1/20
[52] U.S. Cl. .................................. 435/220; 435/71.1; 435/187; 435/188; 435/252.1; 435/253.2; 252/174.12
[58] Field of Search ............ 435/187, 188, 220, 252.1, 435/253.2, 174.2, 71.1; 424/94.64

[56] References Cited
U.S. PATENT DOCUMENTS
3,652,399 3/1972 Isono et al. ..................... 435/223
4,511,490 4/1985 Stanislowski et al. ......... 252/174.12

FOREIGN PATENT DOCUMENTS
0214435 3/1987 European Pat. Off. .
2004328 5/1983 Fed. Rep. of Germany .

OTHER PUBLICATIONS

Miyoshita, K; Mikami, Y.; Arai, T.; International Journal of Systematic Bacteriology, "Alkalophilic Actinomycete", *Nocardiopsisdassonville* subsp. *prosing*. Nov., Isolated from Soil, 34(4), pp. 405–409, 1984.

*Primary Examiner*—Douglas W. Robinson
*Assistant Examiner*—Deborah K. Ware
*Attorney, Agent, or Firm*—Steve T. Zelson; Elias J. Lambiris

[57] ABSTRACT

Novel alkaline serine proteases produced by Nocardiopsis sp. strains, for example by aerobic cultivation of strain 10R (NRRL-18262) and *Nocardiopsis dassonvillei* strain M58-1 (NRRL 18133), the proteases being characterized by a pH optimum of about 8, and by retention of at least 60% of maximum activity at pH 7–11 measured with casein as substrate.

The proteases of the invention may be distinguished from the known protease of the Nocardiopsis strain ZIMET 43647 (of East German 2004328) and known Bacillus and fungal alkaline proteases. The Alkaline proteases of strains 10R and M58-1 may also be distinguished from each other.

The protease preparations of this invention are useful detergent additives for cold water laundering.

7 Claims, 6 Drawing Sheets

PROTEASE

This invention relates to a protease-producing strain of Nocardiopsis, to a process for preparing alkaline protease, to an alkaline protease preparation derived from Nocardiopsis, to a detergent additive and to an enzymatic detergent additive.

BACKGROUND OF THE INVENTION

Proteolytic enzymes produced by cultivation of microorganism strains from the genus Bacillus in suitable nutrient media are widely used in detergent compositions. Examples of such commercially available proteinase products are ALCALASE®, ESPERASE®, SAVINASE®, all supplied by NOVO INDUSTRI A/S, Denmark. These and the similar Bacillus derived enzyme products from other suppliers are enzymatically active in detergent solutions, at pH values in the range of from 8 to 11 and in the presence of the sequestering agents, surfactants and bleaching agents normally present in detergent solutions.

The protease in ALCALASE® is produced by cultivating strains of species *Bacillus licheniformis*. The proteases in ESPERASE® and SAVINASE® are obtainable by cultivation of alkalophilic Bacillus species, such as the strains NCIB 10147 and NCIB 10309, respectively. The temperature optima of the commercially available alkaline proteases is about 60° C. However, these commercial enzymes exhibit a relatively lower activity at room temperature.

BRIEF STATEMENT OF THE INVENTION

This invention relates to the production, isolation, characterization and use of novel alkaline proteases obtained from actinomycete microorganisms. The proteases of this invention are isolated from the actinomycete Nocardiopsis sp. strain 10R and *Nocardiopsis dassonvillei* strain M58-1 which have not been previously known to produce alkaline proteases. The proteases described in this invention are useful as detergent additives for laundering. The strain ZIMET 43647 of the species *Nocardiopsis dassonvillei* described by GDR patent No. DD 200,432 8 is known to produce protease for fibrinolytic and biological-sludge-clarifying applications. However, the strain was not available to the public as of the date hereof, the type strain does not produce protease, and no other strain of this species is known to produce protease. Further the aforementioned patented protease has a temperature profile and pH optimum much different from that of proteases in the invention.

Figure 3:
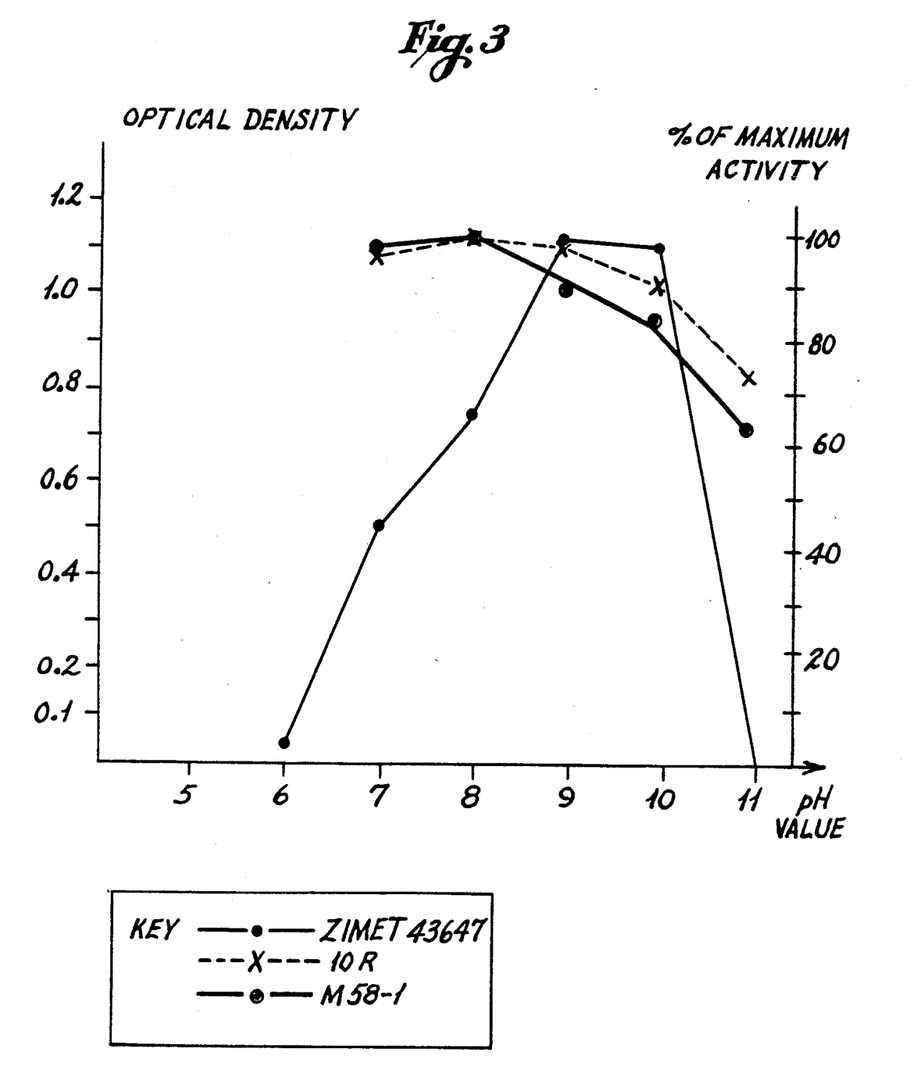
FIGS. 3 and 4 show pH-activity and temperature-activity curves for two proteases of the invention (10R and M58-1), compared with published data for protease ZIMET 43647.

In FIG. 3, the pH profiles for the Nocardiopsis sp. proteases of this invention were compared to that reported for the protease from patent strain ZIMET 43647. Under the same experimental conditions, strains 10R and M58-1 both have pH optima of 8, while that of the ZIMET 43647 protease is 9-10. In addition, the proteases of this invention have broader pH optima, showing at least 60% of the maximum activity between pH 7-11. The ZIMET 43647 protease possesses only 50% of maximum activity at pH 7 and 0% of maximum activity at pH 11. The expression of high proteolytic activity at pH 11 is especially important for detergent application.

Figure 4:
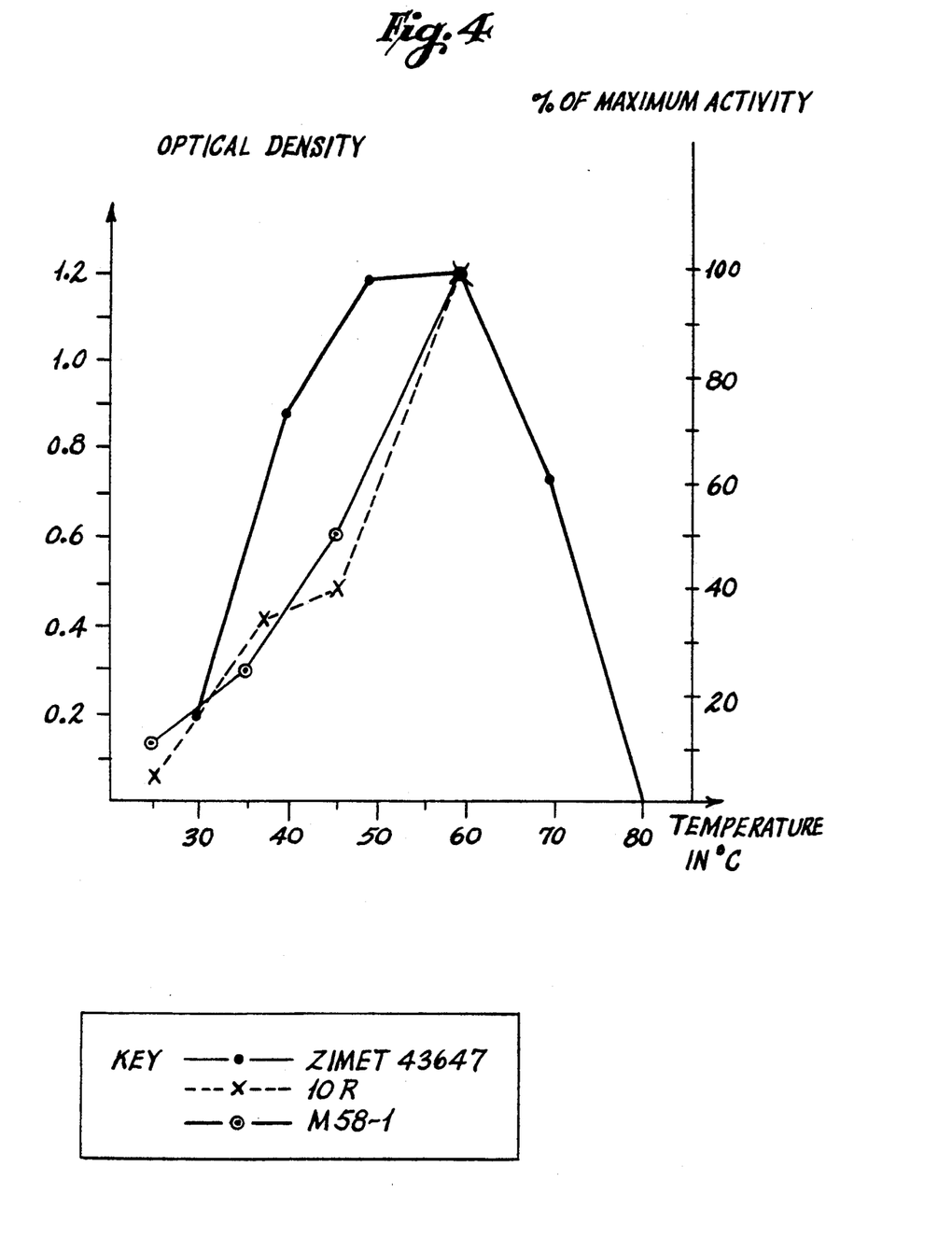

The temperature profiles for the proteases of this invention were compared to that reported for the protease from ZIMET 43647 in FIG. 4. Between 40° and 50° C., the ZIMET 43647 protease exhibits 70-100% of its optimum activity, which is greater than that shown by the proteases of this invention, i.e. 25-65%.

In addition to the aforementioned differences, protease production in the strains of this invention responds differently to the addition of mineral salts. The strains of this invention produce the same level of protease activity whether or not mineral salts are included in the growth medium. The ZIMET 43647 strain is reported to show an improved response upon addition of mineral salts to the growth medium, possibly indicating the presence of a metalloprotease. As shown clearly in FIG. 2b, the protease of this invention has no detectable metalloprotease activity.

The Nocardiopsis sp. strain 10R and *Nocardiopsis dassonvillei* strain M58-1 proteases of this invention are especially effective as detergent additives at low laundering temperature, e.g. in cool water, say 15°-25° C. compared to the commercially available Bacillus proteases. In addition, the Nocardiopsis sp. strain 10R and *Nocardiopsis dassonvillei* strain M58-1 proteases of this invention generate protein hydrolysis patterns different from that generated by a Bacillus protease.

Despite many similarities, i.e. pH and temperature optima, stability, pattern of insulin digestion, the proteases from Nocardiopsis sp. strain 10R and *Nocardiopsis dassonvillei* strain M58-1 can be distinguished. As described in Example V, the molecular weights of the proteases differ (23,500-25,000 for 10R, 20,500 for M58-1). The isoelectric points of the two proteases differ as well—pI $\geq$9.5 for 10R, pI of 9.15 and 8.2 (2 bands) for M58-1. In addition, antibodies to the 10R protease indicate only partial identity to the M58-1 protease and vice versa.

DISCUSSION OF THE INVENTION

There are many current commercial uses for proteases, including utilization in the detergent industry. The detailed discussion of the novel Nocardiopsis sp, strain 10R and *Nocardiopsis dassonvillei* strain M58-1 proteases which follows is limited to usage as a detergent additive. In addition, the inventors do recognize that other uses for proteolytic enzymes do exist.

It should be recognized that enzymes are affected by the conditions of usage, including pH, temperature, and for detergent use, the presence of sequestering agents such as EDTA. In consequence, the Bacillus proteases, such as SAVINASE® which were developed for laundering cotton fabrics at high temperature (60° C.), may not be as effective at the lower wash temperatures (15°-25° C.) recommended for many modern-day fabrics.

Protease preparations comprising the novel alkaline proteases from Nocardiopsis sp. strain 10R and *Nocardiopsis dassonvillei strain M*58-1 exhibit about 20-50% greater capability for whitening protein-based stains on cotton (EMPA 116) under simulated laundering conditions at 15° C. than the SAVINASE® protease when used at the same enzyme activity level, as evidenced in Table IV.

DETAILED DESCRIPTION OF THE INVENTION

According to a further aspect of this invention there is provided a method for producing the alkaline proteases, which process is characterized by cultivating a protease producing strain of Nocardiopsis sp. under aerobic conditions in a nutrient medium containing assimilable sources of carbon, nitrogen, and phosphorus, followed by recovery of the protease preparation from the fermentation broth.

Figure 1:
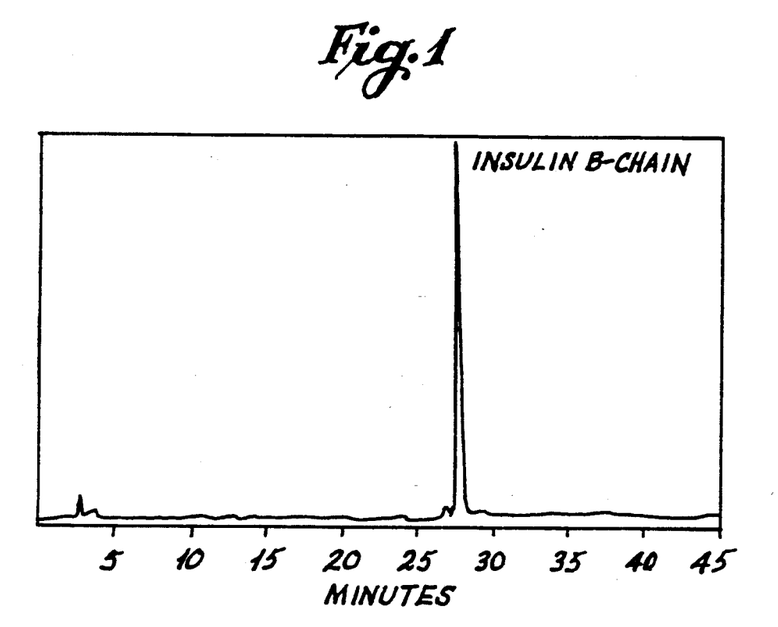
FIG. 1 shows elution chromatograms of digestion products of oxidized B-chain of insulin with 10R protease of the invention. Similar chromatograms are shown for the undigested substrate and after digestion with Savinase ® and Alcalase ® (prior-art proteases).
Figure 1A:
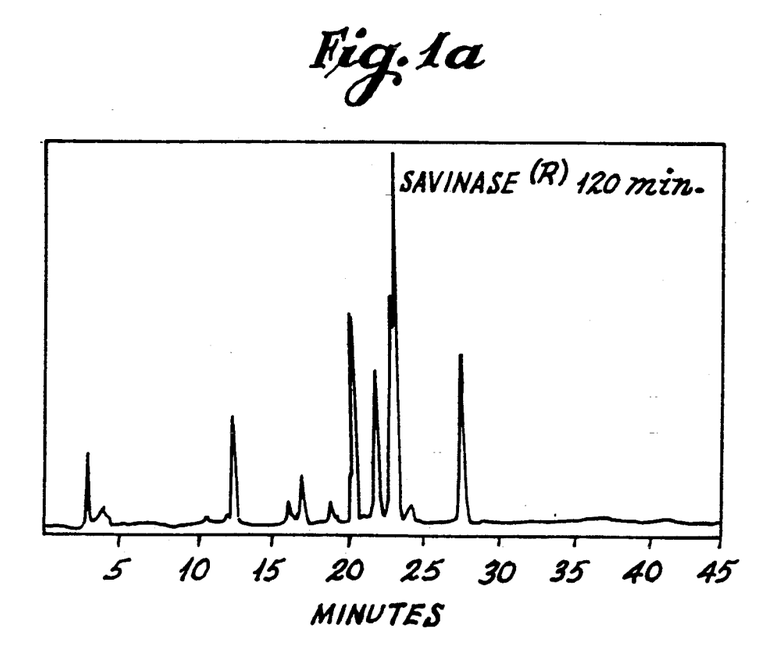
Figure 1B:
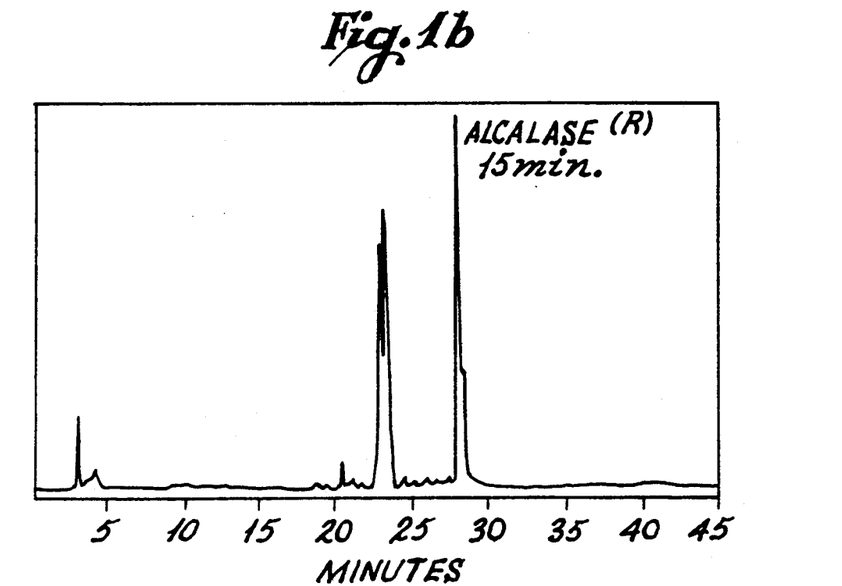
Figure 1C:
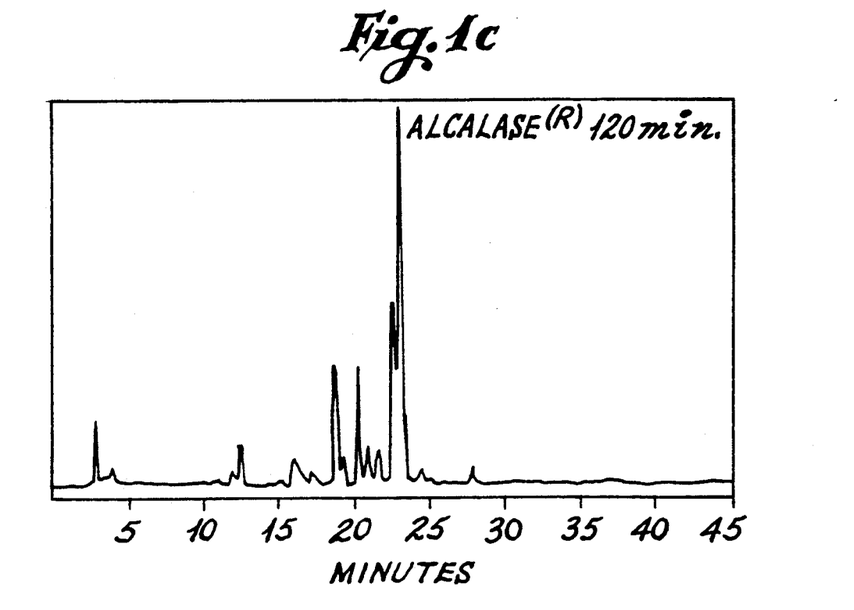
Figure 1D:
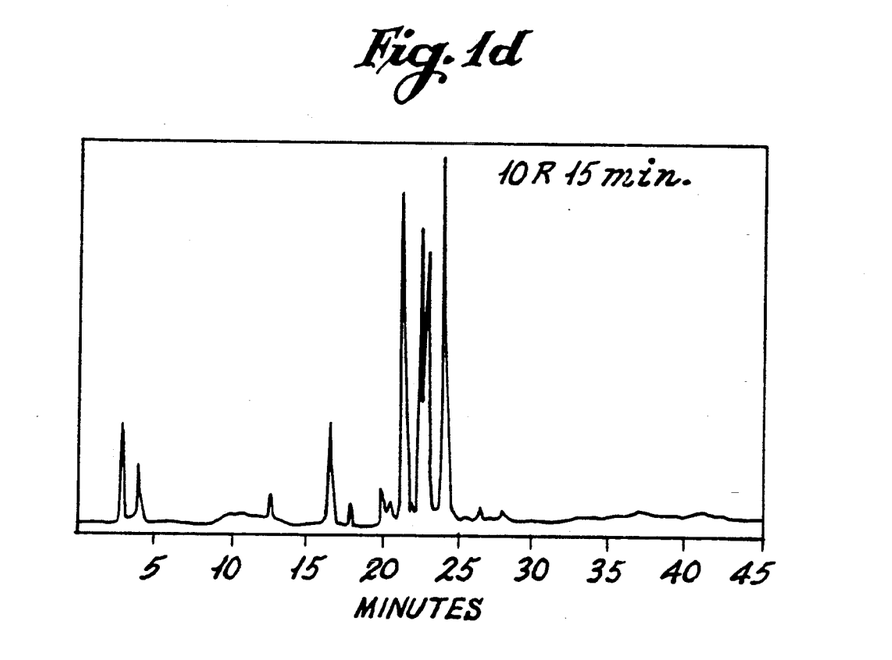
Figure 1E:
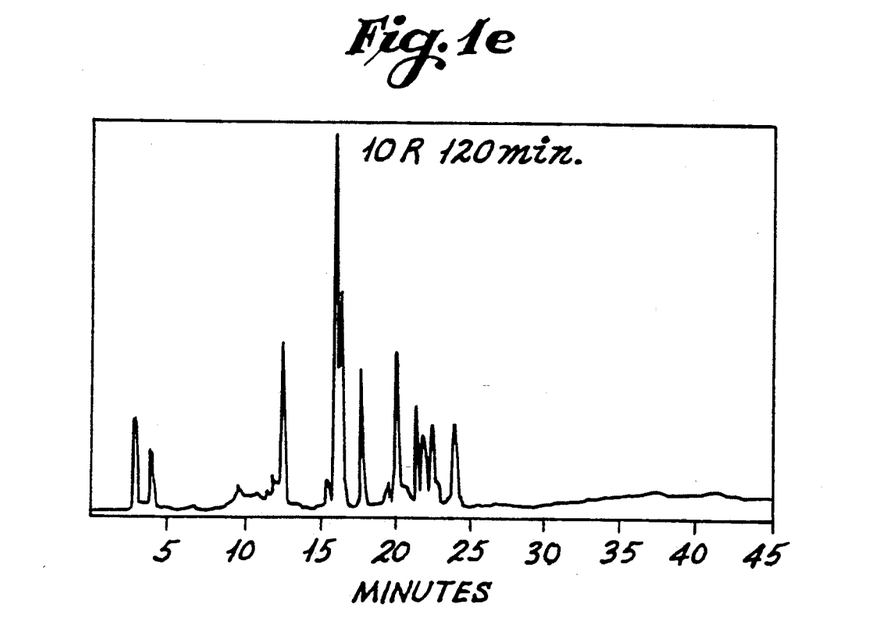

For further understanding of this invention, reference is made to the attached drawings wherein:

FIGS. 1 and 1a show the elution chromatograms of digestion products after 15 minutes and 2.5 hours of treatment of oxidized β-chain of insulin with the Bacillus protease product SAVINASE ®. FIGS. 1b and 1c show the elution chromatograms of digestion products after 15 minutes and 2.5 hours of treatment of oxidized β-chain of insulin with the Bacillus protease product ALCALASE ®. FIGS. 1d and 1e show the elution chromatograms of digestion products after 15 minutes and 2.5 hours of treatment of oxidized β-chain of insulin with the protease from Nocardiopsis sp. strain 10R. The protease from *Nocardiopsis dassonvillei* strain M58-1 yields digestion products that are similar to those for Nocardiopsis sp. strain 10R (data now shown).

Figure 2:
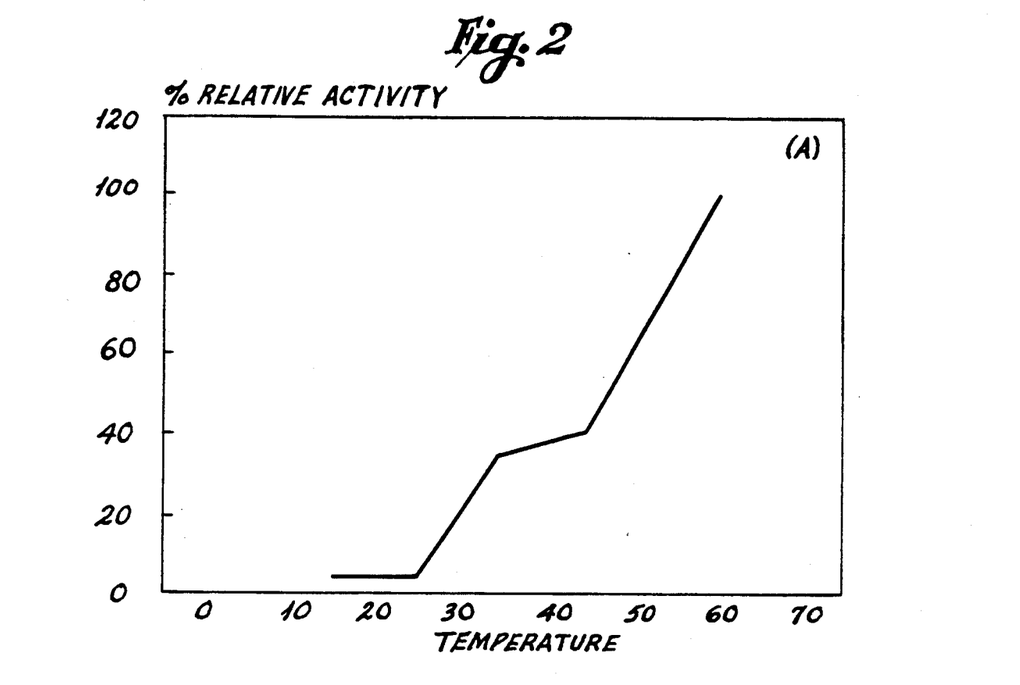
FIG. 2 shows temperature-activity and pH-activity curves for 10R protease of the invention.
Figure 2A:
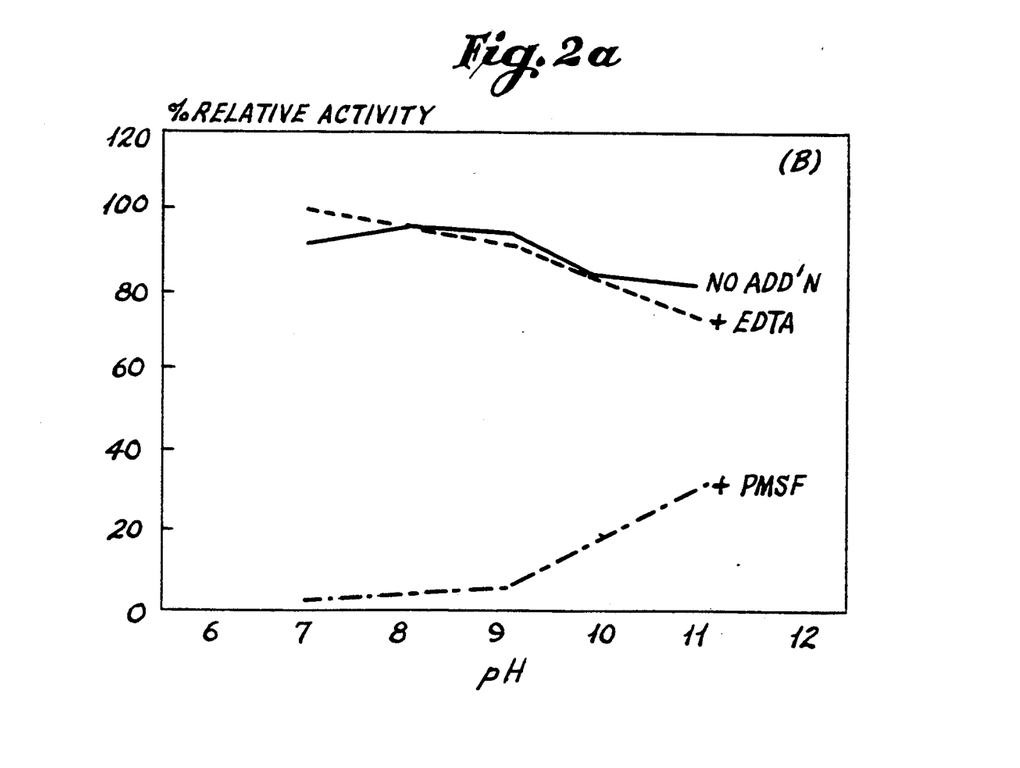

FIG. 2 shows the activity of the protease from Nocardiopsis sp. strain 10R toward casein as a function of temperature. FIG. 2A shows the activity of the same protease toward casein as a function of pH. In addition, the effects of EDTA (10 mM) and phenylmethyl sulfonyl fluoride (PMSF, 1 mM) on protease activity are also presented. The protease from *Nocardiopsis dassonvillei* strain M58-1 behaves similarly to the protease from strain 10R in that PMSF, but not EDTA, inhibits activity. These results indicate that the proteases from strains 10R and M58-1 are serine proteases, not metallo-proteases.

FIG. 3 shows the differences in pH optima of Nocardiopsis sp. strain 10R, *Nocardiopsis dassonvillei* strain M58-1 and patented strain ZIMET 43647.

FIG. 4 presents the differences in temperature optima between Nocardiopsis sp. strain 10R, *Nocardiopsis dassonvillei* strain M58-1 and patented strain ZIMET 43647.

THE MICROORGANISMS

The microorganisms of this invention are aerobic, actinomycete isolates of Nocardiopsis.

Two strains have been deposited at the Agricultural Research Culture Collection (NRRL), Peoria, US, under the terms of the Budapest Treaty, as follows:

| Depositor's reference | 10R | M58-1 |
| --- | --- | --- |
| Deposit No. | NRRL 18262 | NRRL 18133 |
| Deposit date | 10 Nov. 1987 | 13 Nov. 1986 |
| Taxonomic designation | Nocardiopsis sp. | N. dassonvillei |

Mutants and variants of these strains, obtained by methods known in the art, are also within the scope of the invention.

Temperature for growth of both strains is 20° C. to 30° C., no growth at or above 35° C. Optimal pH for growth is 9 and no growth occurs at or below pH 8. The aforementioned growth parameters are different from those of patented strain ZIMET strain 43647. The ZIMET strain is cultivated at a temperature between 25° and 37° C. (preferably 28° C.) and at an acidity of between pH 6.5 and 7.2.

On Czapek Dox Agar slants mature colonies of Nocardiopsis sp. strain 10R exhibit gray-green aerial mycelia with black secretions, *Nocardiopsis dassonvillei* strain M58-1 mature colonies have white to cream colored aerial mycelia on Czapek Dox Agar slants. The typical *Nocardiopsis dassonvillei* species have mealy aerial mycelia with a faint yellow-gray tint.

The type strain of *Nocardiopsis dassonvillei* (ATCC 23218) does not elaborate the protease of this invention. It is believed that the type strain (ATCC 23218) and the Nocardiopsis sp. isolates of this invention are different variants. Moreover, strain 10R and M58-1 are different from each other by the response to the general protoplasting reagents, egg-white lysozyme and NovoZym TM 234. Strain 10R is unable to be lysed by lysozyme and/or NovoZym TM 234 while strain M58-1 can be protoplasted by lysozyme alone. The typical *Nocardiopsis dassonvillei* strains are susceptible to lysozyme (M. C. Shearer et. al., *Int. J. Syst. Batteriol* 33:369–374, 1983). These indicate that the linkages of polypeptidoglycan cell wall of strain 10R are most likely different from those of strain M58-1. Taxonomic analyses of cell wall indicate that there is a good possibility that strain 10R is a new species. More detailed taxonomic identification for strain 10R was underway as of the date hereof.

ASSAY FOR PROTEOLYTIC ACTIVITY

The proteolytic activity in Nocardiopsis sp. cultures was determined by the well known Anson hemoglobin method, cfr. *Journal of General Physiology*, 22, 79–89 (1959). One Anson unit is the amount of proteolytic enzyme digesting hemoglobin at a pH value of 9.0 and a temperature of 25° C. during a reaction time of 10 minutes with such an initial velocity that per minute there is formed such an amount of split products which cannot be precipitated with trichloroacetic acid that these split products give the same color with phenol reagent as does one milli-equivalent of tyrosine.

Proteolytic activity was also determined by the hydrolysis of casein and subsequent reaction of TCA-soluble peptides with o-phthaldialdehyde and 2-mercaptoethanol. The absorbance of the resultant complex is measured at 340 nm and compared to a serine standard. Reaction mixtures are comprised of 1.0 ml of 2.0% (W/V) Hammerstein casein and 0.5 ml of an appropriate enzyme dilution both in Universal Buffer I of Britton and Robinson, pH 9.5 (*J. Chem. Soc.* 1931, p. 1451). Mixtures are incubated for 30 minutes at 25° C. then the reaction terminated by addition of 2.5 mls stop reagent (3.6% W/V trichloroacetic acid, 6.0% W/V sodium acetate and 3.78% v/v glacial acetic acid in deionized water). In control reactions, the stop reagent is added prior to enzyme addition. After 20 minutes at 25° C., the reaction mixtures are filtered through Whatman filter paper #42 or centrifuged.

An aliquot (200 ul) of the filtrate is added to 3 ml of OPA reagent containing 0.05M sodium tetraborate, 1% W/V sodium dodecylsulfate, 0.8 mg/ml O-phthaldialdehyde (OPA) (originally dissolved as a 40 mg/ml solution in ethanol), and 0.2% v/v 2-mercaptoethanol. After 2 minutes, the absorbance at 340 nm is determined. Similarly, a 200 ul aliquot of a serine standard (0.2 mg/ml) is added to 3 ml of OPA reagent and the $A_{340}$ determined. Activity is expressed in CPU (Casein Protease Unit) where 1 CPU is defined as the amount of enzyme which, under standard conditions, produces an amount of non-TCA-precipitable digestion products per minute corresponding to 1 millimole of serine.

PREPARATION OF PROTEASE CONCENTRATE

The Nocardiopsis of the invention may be cultivated under aerobic conditions in a nutrient medium containing assimilable carbon and nitrogen together with other essential nutrients, the medium being composed in accordance with the principles of the known art.

Suitable carbon sources are carbohydrates, such as sucrose, glucose, and maltose, or carbohydrate containing materials such as cereal grains, malt, rice and sorghum. The carbohydrate concentration incorporated in the medium may vary widely, e.g. 1 to 15%, but usually 8-10% will be suitable, the percentage being calculated as equivalents of glucose.

The nitrogen source in the nutrient medium should be of an organic nature. Among the organic nitrogen sources, quite a number are regularly used in fermentation processes involving the cultivation of actinomycetes. Illustrative examples are soybean meal, cotton seed meal, peanut meal, casein, corn steep liquor, yeast extract, and albumin. In addition, the nutrient medium should also contain the usual trace substances.

Since the Nocardiopsis strains of the invention are psychrophilic in that they are unable to grow at temperatures above 35° C., the cultivation is preferably conducted in the temperature range of 20° C. to 30° C. and at alkaline pH values. The alkaline pH may be obtained by addition of suitable buffers, such as sodium carbonate or mixtures of sodium carbonate and sodium bicarbonate (after sterilization of the growth medium). For cultivation in tank fermentors, it is necessary to use artificial aeration. The rate of aeration may be that employed in conventional tank fermentation.

After fermentation, a liquid enzyme product may be produced by removal of coarse material from the broth and, if desired, through concentration of the broth by evaporation at low temperature or by reverse osmosis. Finally, preservatives may be added to the concentrate.

According to the invention, alkaline protease can also be prepared by cultivation of a microorganism containing a gene encoding for and expressing a protease derived from a Nocardiopsis strain of the invention, followed by recovery of the protease from the culture broth. Said microorganism to be cultivated is either the Nocardiopsis strain itself (including mutants and variants), or is a transformed host organism wherein the gene has been inserted by recombinant DNA techniques. Such techniques are known in the art and generally comprise the following steps:

a) providing a suitable recombinant DNA cloning vector comprising DNA-sequences encoding functions facilitating gene expression and a DNA-sequence encoding the Nocardiopsis protease;

b) transforming a suitable host organism with the cloning vector from step a); and c) culturing the transformed host in a suitable culture medium and optionally recovering the protease from the culture medium.

Preferred host organisms are strains of Nocardiopsis Streptomyces, yeast and Aspergillus. It is especially preferred to use *A. oryzae* as the host according to EP 238,023 (Novo).

PEPTIDE MAPPING

The peptides produced by protease-catalyzed digestion of the oxidized B-chain of insulin were separated by reverse phase HPLC. Chromatograms of peptide digestion products obtained through the action of the Nocardiopsis sp. strain 10R protease, purified as described in Example V, are shown in FIG. 1. For comparison, the peptides generated by digestion with the known alkaline proteases, ALCALASE®, ESPERASE®, SAVINASE® are also given. It may be seen that the protease of this invention (10R) is distinctly different from any of the Bacillus alkaline proteases with regard to its pattern of digestion of the oxidized B-chain insulin. In addition, for strain 10R protease the peak which corresponds to intact B-chain insulin on the chromatogram disappears at an earlier time point than with the Bacillus proteases. The protease from *Nocardiopsis dassonvillei* strain M58-1 produces a digestion pattern that is very similar to that of strain 10R (data not shown).

ENZYME PREPARATION

Solid enzyme preparations may be prepared from the purified and/or concentrated broth by precipitation with salts such as $Na_2SO_4$ or with water miscible solvents such as ethanol or acetone. Removal of the water in the broth by suitable drying methods such as spray drying may also be employed. The proteolytic activity of protease preparations so obtained is usually in the range of 0.2-1.0 AU/g. (approx. 0.2-1.0 CPU/g).

The protease preparation of the invention is preferably in a form suitable for use as a detergent additive, particularly a non-dusting granulate, a stabilized liquid or a protected enzyme.

Non-dusting granulates may be produced e.g. according to NL 167,993 (Novo), U.S. Pat. Nos. 4,106,991 (Novo) or 4,661,452 (Novo) and may optionally be coated according to principles known in the art.

A liquid protease preparation may be stabilized e.g. by adding propylene glycol, other polyols, sugars, sugar alcohols and boric acid. Other enzyme stabilizers are known in the art.

Protected enzyme may be produced according to EP 238,216 (Novo, Albright & Wilson).

DETERGENT COMPOSITION

The detergent compositions of the invention comprise surfactant which may be of the anionic, non-ionic, cationic or zwitterionic type, or a mixture of these. Typical examples of anionic surfactant are linear alkyl benzene sulfonate (LAS), alpha olefin sulfonate (AOS), alcohol ethoxy sulfate (AES) and natural soap of alkali metals.

Detergent according to the invention may contain other detergent ingredients known in the art, such as builders, bleaching agents, bleach activators, anti-corrosion agents, sequestering agents, anti-soil redeposition agents, perfumes, stabilizers for the enzymes and bleaching agents and so on.

The detergent compositions of the invention can be formulated in any convenient form, such as powders, liquids, etc. The protease may be stabilized in a liquid detergent by inclusion of enzyme stabilizers, e.g. those mentioned above.

Detergents usually have a pH in solution of 7-12, especially 8-10.5. Due to its broad pH optimum, protease of the invention is highly active in this whole range.

The detergent of the invention may include one or more other detergent enzymes in addition to protease of the invention. Examples are lipase, amylase, cellulase and protease (other than protease of the invention), e.g. alkaline Bacillus protease. The two (or more) enzymes

EXAMPLE I

Nocardiopsis sp. strain 10R was cultivated at 30° C. on a rotary shaking table (250 rpm) in 250 ml triple-baffled Erlenmeyer flasks containing 50 ml of medium of the following composition:

| | |
|---|---|
| Maltodextrin M-100 | 20 |
| Soy bean flour | 20 |
| Yeast Extract | 2 |
| $K_2HPO_4$ | 9 |
| $CaCO_3$ | 5 |

After sterilization, the pH of the medium was adjusted to 9.0 by the addition of 5 ml of 1M solution of sodium carbonate/sodium bicarbonate buffer, pH 9.2. After 2 to 5 days of incubation, the proteolytic activity of the broth was determined using the Anson assay method described above. The enzyme activity of the 10R broth was 13.3 AU/1 after 93.5 hours incubation.

*Nocardiopsis dassonvillei* strain M58-1 was cultivated as described, except that incubation was at 25° C. After 140.5 hours of incubation, the broth had an enzyme activity of 9.6 AU/1.

EXAMPLE II

Nocardiopsis sp. strain 10R was cultivated in the medium and under conditions as described in Example I. After 26 hours of growth, 2 liters of the culture were used to inoculate 50 liters of the described medium in Example I in a fermentor, of which the pH of the medium was not controlled after sterilization.

After inoculation, the growth pH of the fermentor was controlled at 8.7 with 2M $Na_2CO_3$ and 10% $H_3PO_4$. Temperature was maintained at 30° C. After 90 hours, protease titer was determined using the Anson assay method, a value of 11.5 Anson units/liter being indicated.

The culture broth was centrifuged to remove cells. Supernatant was then filtered (0.45μ) and concentrated by ultrafiltration (10,000 molecular weight cut-off) to become the product employed in the following examples.

*Nocardiopsis dassonvillei* strain M58-1 was cultivated in the medium and under conditions as described in Example I, except the incubation temperature was at 25° C. After 24 hours of growth, 2 liters of the culture were used to inoculate 50 liters of the fermentor medium consisting of the following components (grams/liter):

| | |
|---|---|
| Maltodextrin | 40 |
| Cerelose | 40 |
| Soy bean flour | 60 |
| $K_2HPO_4$ | 5.5 |
| $MgSO_4$ | 0.40 |
| $CaCl_2$ | 0.30 |
| Trace mineral solution | 7 ml |

The temperature of the fermentation was controlled at 30° C. The initial pH was set at 8.6 and was controlled not to fall below 8.5 by addition of 2M $Na_2CO_3$ and not to exceed 8.8 by addition of $H_3PO_4$. A glucose feed was started when glucose was depleted and the percent D.O. began to rise. The feed stream consisted of a glucose solution (500 g cerelose in 500 g $H_2O$). The glucose was fed at a constant rate of 3.5 ml/liter/hr until 20 g/liter glucose had been added (approximately 12 hours).

Protease began to accumulate at 40 hours with a peak titer of 53 AU/1 obtained at 120 hours.

The culture broth was centrifuged to remove cells. Supernatant was then filtered (0.45μ) and concentrated by ultrafiltration (10,000 molecular weight cut-off) to become the product employed in the following examples.

EXAMPLE III

The protease activity of strain 10R from Example II as a function of pH and temperature was determined by using casein as the substrate according to the assay method described previously. In addition, the effects of EDTA (10 mM) and phenylmethylsulfonyl fluoride (PMSF, 1 mM) on protease activity were examined. Results are depicted graphically in FIG. 2. As seen in FIG. 2 (a), the temperature optimum is greater than or equal to 60° C., similar to the commercial protease Alcalase. The protease shows maximal activity between pH 8-9 and at least 85% of the maximum in the pH range 7-11. EDTA has no effect on protease activity, while the addition of PMSF results in almost complete inhibition, indicating that the protease is of the serine type.

EXAMPLE IV

The stability of proteases from strains 10R and M58-1 in the presence of various detergent components at 25° C. or 40° C. was determined as follows:

Proteases were diluted to 0.5 AU/1 in 0.01M borate buffer, pH 9.5 with or without the additional components shown in Table I. The samples were incubated at 25° C. or 40° C. for 30 minutes, then assayed at 25° C. for protease activity. Results are shown in Table I.

Both of the Nocardiopsis sp. proteases tested retained at least 83% of their original activities at either 25° C. or 40° C., thus making them suitable for laundering use.

TABLE I

Stability of Proteases from Nocardiopsis sp. 10R and *Nocardiopsis dassonvillei* M58-1 in the Presence of Detergent Components

| | % Activity Remaining Incubation Conditions | | | | | | | |
|---|---|---|---|---|---|---|---|---|
| | 25° C. | | | | 40° C. | | | |
| Enzyme | no add'n | 10 mM CaCl₂ | 10 mM EDTA | 0.1% STPP* | no add'n | 10 mM CaCl₂ | 10 mM EDTA | 0.1% STPP |
| 10R | 100 | 90 | 94 | 94 | 101 | 83 | 95 | 98 |
| M58 | 100 | 102 | 102 | 98 | 105 | 110 | 105 | 111 |

*STPP is sodium tripolyphosphate

EXAMPLE V

The protease from Nocardiopsis sp. strain 10R prepared in Example II was purified as follows:

Concentrated cell-free broth was first loaded onto a Sephadex-G25 column (medium grade) equilibrated in 0.05M HEPES, pH 7 buffer. Protein was eluted from the column in the same buffer and fractions containing protease activity were pooled. If necessary, the pooled enzyme solution was diluted with water or buffer to give an appropriate ionic strength, then was loaded onto a CM-Sepharose Fast Flow column equilibrated in 0.05M HEPES, pH 7. Approximately 50% of the total protease activity bound to the resin and was subsequently eluted with a linear salt gradient (0–75 mM NaCl).

The CM-Sepharose purified protease possessed a specific activity of 21.0 AU/g (15 CPU/g).

When analyzed by SDS-PAGE, the purified protease was shown to contain two components, one major and one minor with molecular weights of 25,000 and 23,500, respectively. Protease from *Nocardiopsis dassonvillei* strain M58-1 purified in a similar manner consisted of one band on SDS-PAGE with molecular weight of 20,500.

TABLE II

Summary of Purification of Strain 10R Protease

| Step | AU/l | Total AU | Total Recovery (%) | Specific Activity (AU/g) | Fold Purification |
|---|---|---|---|---|---|
| Crude cell-free concentrate | 19.4 | 0.97 | 100 | — | — |
| Sephadex-G25 | 16.8 | 0.89 | 92 | 6.2 | 1.0 |
| CM-Sepharose | 2.29 | 0.44 | 45 | 21.0 | 3.4 |

EXAMPLE VI

Proteases from Nocardiopsis sp. were distinguished from the commercial proteases ALCALASE®, SAVINASE®, and ESPERASE® by their pattern of digestion of the oxidized B-chain of insulin. Protease ($2.7 \times 10^{-5}$ CPU) was added to oxidized B-chain of insulin (0.17% w/v) in pH 9.0 buffer and incubated for 15 minutes or 2.5 hours at 25° C. After boiling 20 minutes to quench the reactions, samples were injected onto a reverse-phase HPLC column (Bakerbond Widepore C₁₈) equilibrated in 0.1M ammonium sulphate, pH 3. Peptides were eluted with a linear gradient of 0–50% acetonitrile.

Chromatograms are shown in FIG. 1 and indicate that the protease of this invention is distinct from any of the Bacillus alkaline proteases with regard to its pattern of digestion of the oxidized insulin B-chain. In addition, for strain 10R protease, the peak which corresponds to intact B-chain insulin on the chromatogram disappears at an earlier time point than with the Bacillus proteases.

EXAMPLE VII

Washing tests were performed in a Terg-O-Tometer for ten minutes at 15° C. with EMPA 116 test fabric swatches (cotton soiled with blood, milk, and carbon black) supplied by Test Fabrics, Inc., Middlesex, N.J. Enzyme dosages of 0.025, 0.05, 0.1 CPU/l were added to Tide® (<0.5% phosphate, no enzymes, pH 10.4). The proteases used were from strain 10R and SAVINASE®.

The cleaning ability of the proteases was measured by reflectance change ($\Delta R$), i.e. the reflectance value of enzyme-washed test swatches minus that of swatches washed without enzyme. Reflectance values were read with the aid of a Gardiner Reflectometer XL 800 (Bethesda, Md.).

The results are shown in Table III. They indicate that it is possible to obtain 20–50% greater cleaning ability with 10R protease than with Savinase at the same dosage.

TABLE III

Wash Efficacy of 10R Protease and Savinase on EMPA 116

| Enzyme | Dose (CPU/l) | Reflectance Change ($\Delta R$) | % Increase |
|---|---|---|---|
| 10R | 0.025 | 3.9 | 50% |
| | 0.05 | 7.1 | 29% |
| | 0.10 | 11.5 | 20% |
| Savinase | 0.025 | 2.6 | — |
| | 0.05 | 5.5 | — |
| | 0.10 | 9.6 | — |

TABLE IV

Wash Efficacy of Nocardiopsis sp. Strain 10R and *Nocardiopsis dassonvillei* Strain M58-1 Proteases on EMPA 116, Spinach, and Blood Stains

| Protease | Reflectance Change ($\Delta R$) | | |
|---|---|---|---|
| | EMPA 116 | Spinach | Blood |
| 10R | 7.3 | 4.7 | 8.2 |
| M58-1 | 9.7 | 3.1 | 6.8 |
| Savinase® | 5.7 | 3.5 | 2.8 |
| Alcalase® | 2.7 | 3.1 | 5.5 |

EXAMPLE VIII

Washing tests were performed using proteases from Nocardiopsis sp. strain 10R and *Nocardiopsis dassonvillei* strain M58-1 and, for comparison, the commercial proteases ALCALASE® and SAVINASE®. EMPA 116 test fabric swatches (cotton soiled with blood, milk, and carbon black) were supplied by Test Fabrics, Ind., Middlesex, N.J.; spinach and blood swatches were made in-house by applying fresh spinach extract or bovine blood to desired cotton fabric then air-drying. Wash tests were performed in a Terg-O-Tometer for ten minutes at 15° C. in a detergent of the following composition:

| Component | g/l |
| --- | --- |
| LAS (Nansa 80 S, 80% active) | 0.4 |
| AE (Berol 065) | 0.15 |
| Soap (Sumlight, 80% active) | 0.15 |
| Sodium tripolyphosphate | 1.75 |
| Sodium silicate | 0.4 |
| Carboxymethyl cellulose | 0.05 |
| EDTA | 0.01 |
| Sodium sulfate | 2.1 |
| Water | |
| Adjusted to 9° dH German hardness, pH 9.5. | |

An enzyme dosage of 0.05 CPU/1 was used with EMPA and spinach stains, 0.5 CPU/1 with the blood stain.

Reflectance values were read with the aid of a Gardiner Reflectometer XL 800 (EMPA and spinach) or an Elrepho 2000 at 460 nm (blood). The cleaning ability of the proteases was measured by reflectance change (Δ R), i.e. the reflectance value of enzyme-washed test swatches minus that of swathes washed without enzyme. The results are compiled in Table IV.

It is evident from the results that the Nocardiopsis sp. strain 10R and *Nocardiopsis dassonvillei* strain M58-1 proteases show equivalent to superior performance based on equal dosage on all types of stain tested. In particular, protease from strain M58-1 is the preferred enzyme for use on EMPA 116, protease from strain 10R is preferred for use on blood stains.

We claim:

1. A detergent additive, comprising an alkaline serine protease derived from a strain of Nocardiopsis, having a pH optimum of about 8 and retaining at least 60% of maximum activity at pH 7-11 measured with casein as the substrate, said additive being in the form of a non-dusting granulate or a stabilized liquid.

2. The detergent additive according to claim 1, wherein the strain of Nocardiopsis is 10R, M58-1, or a mutant thereof capable of producing the alkaline serine protease.

3. The detergent additive according to claim 2 having a proteolytic activity of 0.5-10 CPU/g.

4. A detergent composition, comprising (a) an alkaline serine protease derived from a strain of Nocardiopsis, having a pH optimum of about 8 and retaining at least 60% of maximum activity at pH 7-11 measured with casein as the substrate and (b) a surfactant.

5. The detergent composition according to claim 4 having a proteolytic activity of 0.001-0.5 CPU/g.

6. A process for preparing an alkaline serine protease, comprising (a) cultivating a strain of Nocardiopsis aerobically under submerged conditions in a nutrient solution containing suitable carbon and nitrogen sources at an alkaline pH and a temperature in the range of 20°-30° C. and (b) recovering the alkaline serine protease from the culture broth, wherein the alkaline serine protease has a pH optimum of about 8 and retains at least 60% of maximum activity at pH 7-11 measured with casein as the substrate.

7. The process according to claim 6, wherein the strain of Nocardiopsis is 10R, M58-1 or a mutant thereof capable of producing the alkaline serine protease.

* * * * *